United States Patent [19]
Koehler et al.

[11] Patent Number: 6,140,514
[45] Date of Patent: Oct. 31, 2000

[54] PROCESS FOR THE PREPARATION OF MACROCYCLIC ESTERS OR LACTONES

[75] Inventors: Guenther Koehler, Marl; Juergen Chlench, Dorsten, both of Germany

[73] Assignee: Huels Aktiengesellschaft, Marl, Germany

[21] Appl. No.: 09/261,133

[22] Filed: Mar. 3, 1999

[30] Foreign Application Priority Data

Mar. 3, 1998 [DE] Germany .............................. 198 08 845

[51] Int. Cl.$^7$ .................................................. C07D 313/00
[52] U.S. Cl. ............................................. 549/266; 554/124
[58] Field of Search .............................. 549/266; 554/124

[56] References Cited

U.S. PATENT DOCUMENTS 5,717,111  2/1998  Koehler et al. ......................... 549/266

*Primary Examiner*—Amelia Owens
*Attorney, Agent, or Firm*—Oblon, Spivak, McClelland, Maier & Neustadt, P.C.

[57] ABSTRACT

A process for the preparation of macrocyclic esters or lactones in a two-stage reaction, which entails effecting linear oligomerization of monomers having a number of carbon atoms corresponding to the macrocycle and effecting cyclizing deoligomerization, wherein both steps are conducted in the presence of a complex compound of trivalent iron.

20 Claims, No Drawings

PROCESS FOR THE PREPARATION OF MACROCYCLIC ESTERS OR LACTONES

BACKGROUND OF THE INVENTION

1. Field of the Invention

The present invention relates to an improved two-stage process for the preparation of macrocyclic esters or lactones from dicarboxylic acids or dicarboxylic acid dialkyl esters and diols or from hydroxycarboxylic acids using a novel catalyst. The present invention also relates to the second stage of the process separately.

2. Description of the Background

Macrocyclic esters and lactones play an important role in the fragrance industry because of their known musk or ambergris note and also as fixatives. The 13- to 18-membered ring systems are the most widely used.

It is known that macrocyclic lactones can be prepared by a two-stage reaction in which a linear oligoester or polyester is first prepared, and then cyclized by thermal depolymerization. The depolymerizing cyclization is described, for example, in J. Am. Chem. Soc. 57 (1935), 929–34 and in U.S. Pat. No. 4,175,321.

The processes for the preparation of the oligoesters or polyesters in the first stage, employ dicarboxylic acids and diols as starting materials, and usually proceed at from 120 to 200° C., and in most cases without catalyst. For example, the process of DE 32 25 431 uses only the acidity of the dicarboxylic acid, omitting an acidic catalyst, and accepts with long reaction times are required. The processes of DE-A 28 40 905 and of U.S. Pat. No. 4,393,223 employ an acidic fixed-bed catalyst. Prior to the depolymerization stage, it is, however, necessary to add a further catalyst because the effectiveness of the acidic fixed-bed catalyst in the subsequent depolymerization stage is limited.

The cyclizing depolymerization of the second stage is described, for example, in J. Am. Chem. Soc. 57 (1935), 929–34 and in U.S. Pat. No. 4,175,321, and is carried out in the presence of a catalyst and generally at temperatures of from 200 to 300° C. The macrocycles which form have a relatively high vapor pressure under these conditions, whereby it is possible to remove them from the reaction mixture or the reactor by distillation. A large number of catalysts for this stage are known, for example Lewis acids, alkali metal alkoxides and alkaline earth metal alkoxides, oxides, hydroxides and salts of, for example, halohydric acids, nitric acid, carbonic acid, boric acid and of carboxylic acids. Some of the parent acids of the salts are also suitable as a catalyst. Suitable cationic constituents of the salts are alkali metals, alkaline earth metals and heavy metals, such as iron, copper, lead, zinc, tin, nickel, titanium and zirconium.

In processes in which the starting materials are dicarboxylic acid dialkyl esters and diols, and which thus prepare the oligoesters or polyesters by transesterification, catalysts which have proven successful are alkyl stannates, titanates and zirconates (see DE 32 254 31, DE 28 409 05). They are also suitable as catalysts for the depolymerizing cyclization. These compounds do, however, have a relatively high vapor pressure and can only be separated off from the macrocyclic esters or lactones with difficulty. Since they are also transesterification catalysts, their presence even in concentrations of a few ppm during distillation or storage leads to linear oligomers or polymers.

Thus, a need exists for a process for producing macrocyclic esters or lactones, which overcomes the above disadvantages.

SUMMARY OF THE INVENTION

Accordingly, the present invention provides a process for preparing macrocyclic esters or lactones in a two-stage reaction by linear oligomerization of monomers having an appropriate number of carbon atoms and cyclizing deoligomerization, wherein both steps are carried out in the presence of a complex compound of trivalent iron.

DESCRIPTION OF THE PREFERRED EMBODIMENTS

The present process advantageously produces macrocyclic esters or lactones in excellent yields, which are obtained by distillation under reduced pressure in very pure form suitable for use in the fragrance industry. The catalyst of the present invention is nonvolatile under the reaction conditions, whereby the purification distillation is not impaired by catalytic reverse reaction to open-chain oligoesters or polyesters. The cyclizing deoligomerization of the oligoesters in the second stage can be elegantly coupled with their preparation in the first stage since the complex compounds of the trihydric iron are both esterification catalysts and also transesterification catalysts.

The macrocyclic esters or lactones may include from 10 to 24 ring members. However, it is preferred that these macrocycles have from 13 to 18 ring members as they are particularly useful in the fragrance industry. The preferred macrocyclic lactones having from 13 to 18 ring members are obtained from omega-hydroxycarboxylic acids having from 12 to 17 carbon atoms. Alternatively, macrocyclic esters (or dilactones) are obtained from dicarboxylic acids or dicarboxylic acid dialkyl esters and diols, in which case these monomers must be selected such that dilactones having the desired number of ring members can be produced. Dilactones having 14 ring members are obtained, for example, from linear oligoesters, which are formed from adipic acid and 1,6-hexanediol. Dodecanedioic acid and ethylene glycol produce a macrocyclic dilactone having 16 ring members. The macrocyclic esters or lactones can be formed from monomers which, apart from the hydroxyl and carboxyl groups, have a saturated hydrocarbon structure. They may, however, also contain oxygen or nitrogen atoms.

Hydroxycarboxylic acids suitable for the process of the invention have, for example, from 8 to 20 carbon atoms between the functional groups. Examples thereof are, inter alia, omega-hydroxycarboxylic acids, such as 11-hydroxydodecanoic acid, 12-hydroxytridecanoic acid, 15-hydroxyhexadecanoic acid, 17-hydroxyoctadecanoic acid and 11-hydroxy-10-methyldodecanoic acid. Suitable dicarboxylic acids have, for example, from 4 to 20 carbon atoms between the carboxyl groups. Examples thereof are, inter alia, succinic acid, adipic acid, suberic acid, sebacic acid and 1, 12-dodecanedioic acid. Of the suitable diols, which may contain, for example, from 2 to 12 carbon atoms between the hydroxyl groups, the following examples may be mentioned: ethylene glycol, 1,3-propanediol, 1,4-butanediol and-1,6-hexanediol, 1,8-octanediol and 1,12-dodecanediol. As mentioned, as well as containing the oxygen atoms originating from the condensation reaction of carboxyl and hydroxyl groups, the macrocycles may also contain other heteroatoms in the ring. For these, then, dicarboxylic acids, diols and/or lactones having the appropriate heteroatoms are used.

A most important feature of the present process is the use of a complex iron(III) compound as catalyst in both stages of the process. Particularly effective iron(III) complexes are those with chelate complexing agents having bidentate ligands. Of the suitable chelate complexing agents, the following examples may be mentioned: 1,3-dicarbonyl compounds, such as acetylacetone and acetoacetic acid esters; ethylenediaminetetraacetic acid (EDTA), nitrilotriacetic acid ETA), potassium hexacyanoferrate(III) and ethylene glycol bis(2-aminoethyl)tetraacetic acid. Preference is given to NTA and acidic or neutral alkali metal salts thereof. The iron(III) complexes are known substances and are prepared, advantageously in aqueous medium, directly from iron(III) salts and the complexing agents. They are advantageously used in amounts of from 0.1 to 1% by weight, based on the starting materials for the linear oligomers, as a single charge at the start of the reaction in the first stage, in two portions at the start of the reaction in each of the two stages or alternatively divided into smaller portions or continuously throughout the two stages.

In the first stage of the process of the invention, the monomers are converted into linear oligoesters which preferably have a (mean) molecular weight of from about 400 to about 10,000, determined by gel permeation chromatography using polystyrene as the standard. Depending on the starting materials and the amount of catalyst, the process is advantageously carried out at a temperature of from about 50 to 300° C., under atmospheric pressure, reduced pressure or elevated pressure of from about 0.01 hPa to 10 MPa. In order to improve the progress of the reaction or the solubility of the reactants, an inert solvent may be used concomitantly. In the preparation of macrocyclic esters (or dilactones), it is possible to control the molecular weight in a known manner by varying the molar ratio of dicarboxylic acid to diol. The diol is advantageously used in a relatively large molar excess, for example from about 3:1 to 20:1. In the preparation of macrocyclic lactones from hydroxycarboxylic acids, it is possible to control the molecular weight by the duration of the reaction and/or by dilution with a high-boiling inert solvent, for example a polyethylene glycol dialkyl ether. For any given system the parameters by which it is possible to achieve a desired molecular weight can be readily determined by exploratory experiments.

In the first stage of the process, instead of the iron(III) complex, it is also possible to use a customary acidic catalyst, for example an acidic inorganic or organic ion exchanger, which is removed prior to entry into the second stage, for example, by filtration. Although it is necessary to change the catalyst then, it is, however, still advantageous as compared to the mentioned, hitherto preferred tin, titanium and zirconium catalysts as there is no possibility of subsequent polymerization of the macrocyclic reaction product.

In the second stage of the process of the present invention, the linear oligoester is heated in the presence of the iron(III) complex to a temperature of from about 150 to 300° C., advantageously at a pressure of from about 0.01 to 700 hPa. Pressure and temperature are correlated such that the resulting macrocycle and possible solvent and also possible excess reactants, e.g. diol, distill off. The macrocyclic compound can be obtained in high purity from the distillate by renewed distillation.

The reaction in the two stages or in one of the two stages can be carried out batchwise or continuously. For batchwise preparation, it is carried out in, for example, a stirred vessel with attached distillation column. The reaction can be carried out continuously, by passing the reactants and the catalyst under a suitable pressure through appropriately heated reaction zones and distilling off the reaction mixture continuously.

Reference will now be made to certain examples which are provided solely for purposes of illustration and are not intended to be limitative.

EXAMPLE 1

1.1 Preparation of the oligoester 300 g of dimethyl dodecanedioate (1.16 mol) and 600 g of ethylene glycol (9.7 mol) and 0.3 g of the monosodium salt of the iron(III) ethylenediaminete-traacetic acid complex are heated to 180° C. in a 21 glass flask fitted with stirrer and distillation attachment. From about 70 to 74 g of methanol distill off under atmospheric pressure over the course of from 3 to 4 h. The reaction can be monitored by means of gas chromatography. This method produces an oligoester which has a melting range of from 40 to 50° C. and a mean molecular weight of about 600.

1.2 Cyclization stage

The reaction mixture from the first stage is now heated slowly to 250° C. At the same time, the pressure is gradually reduced to 15 hPa. Ethylene glycol and the cyclic ethylene glycol dodecanedioate distill off. Further distillation of the distillate produces 180 g of pure ethylene glycol dodecanedioate, corresponding to a yield of 95%.

EXAMPLE 2

2.1 Preparation of the oligoester 586 g of dimethyl brassylate (2.15 mol) and 294 g of ethylene glycol (4.74 mol) and 1.6 g of tris(2,5-pentadianato)iron(III) (0.005 mol) are heated in a 21 glass flask fitted with stirrer and distillation attachment. The reaction temperature is maintained in the range from 150° C. to 250° C. for 4 h. About 134 g of methanol (about 4.2 mol) distill off under atmospheric pressure (?) over the course of from 3 to 4 h to give 746 g of oligoester having a mean molecular weight of about 600 and a melting range from 40 to 50° C.

2.2 Cyclization stage 300 g of polyethylene glycol dimethyl ether having a molecular weight of about 2000 are heated to 280° C. at a pressure of 10 hPa in a 11 glass flask fitted with stirrer and distillation attachment. 746 g of the oligoester heated to 170° C., which are mixed with 1500 g of ethylene glycol, are metered into the mixture over the course of 8 h. Shortly after metering in has started, ethylene brassylate and ethylene glycol distill off as a mixture. This mixture separates into two phases. The upper ethylene brassylate-containing phase is subjected to purification by distillation to give 540 g of pure ethylene brassylate. The lower ethylene glycol-containing phase from the phase separation is recycled to the first stage for the preparation of the oligoesters. The yield is 92% of theory, based on dimethyl brassylate used.

EXAMPLE 3

3.1 Preparation of the oligoester 399 g of dodecanedioic acid (12.1 mol), 1.653 g of ethylene glycol (26.6 mol) and 1.65 g of potassium hexacyanoferrate(III) (0.05 mol) are stirred at from 170 to 200° C. for 4 h in a 21 glass flask. A gentle stream of nitrogen is passed through the mixture, from which about 33 g of water condense out. The resulting oligoester has a mean molecular weight of about 800 and a is melting point of from 50 to 55° C.

3.2 Cyclization stage 300 g of polyethylene glycol dimethyl ether having a molecular weight of about 2000 are heated to 260° C. at a pressure of 1 hPa in a 11 glass flask fitted with stirrer and distillation attachment. 1.017 g of the oligoester are metered into the mixture over the course of 4 h. Shortly after the metering in has started, the cyclic ethylene glycol dodecanoate together with ethylene glycol distill over. This mixture separates into two phases. The upper ethylene glycol dodecanoate-containing phase is subjected to purification by distillation to give 314 g of pure ethylene glycol dodecanedioate, corresponding to a yield of 95% of theory, based on dodecanedioic acid used.

EXAMPLE 4

In a first stage, an oligoester of 15-hydroxypentadecanoic acid having an average degree of oligomerization of 3.5 is prepared, the monosodium salt of the iron(III) complex of ethylenediaminetetraacetic acid being used as catalyst. In the second stage, 240 g of oligoester, which comprise 0.5 g of said Na salt, together with 300 g of polyethylene glycol diethyl ether having a mean molecular weight of about 2000 are heated to 300° C. at a pressure of 2 hPa in a 1 l reactor. After about 4 h, 214 g of cyclopentadecnolide distill off, which correspond to a yield of about 98% of theory, based on 15-hydroxypentadecanoic acid used.

Having described the present invention, it will now be apparent to one of ordinary skill in the art that many changes and modifications may be made to the above-described embodiments without departing from the spirit and the scope of the present invention.

What is claimed is:

1. A process for preparing a macrocyclic ester or lactone in a two-stage reaction, which comprises reacting in a first stage, a dicarboxylic acid or a dicarboxylic acid dialkyl ester with a diol to form a linear oligoester or reacting a hydroxycarboxylic acid to form a linear oligoester, and then in a second stage, heating the linear oligoester to prepare the macrocyclic ester or lactone by a cyclizing reaction, wherein both stages are conducted in the presence of a complex compound of trivalent iron.

2. The process of claim 1, wherein the macrocyclic compound has from 10 to 24 ring members.

3. The process of claim 2, wherein the macrocycle compound has from 13 to 18 ring members.

4. The process of claim 1, wherein said first stage linear oligomerization affords a linear oligoester having a mean molecular weight of from about 400 to 10,000, determined by gel permeation chromatography using polystyrene as a standard.

5. The process of claim 1, wherein said first stare linear oligomerization is effected at a temperature of from about 50° to 300° C.

6. The process of claim 1, wherein said first stage linear oligomerization comprises reacting a dicarboxylic acid and diol in a molar ratio of from about 3:1 to 20:1, respectively.

7. The process of claim 1, wherein said cyclizing reaction comprises heating a linear oligoester at a temperature of from about 150° to 300° C.

8. The process of claim 1, wherein said complex compound of trivalent iron comprises a chelate complexing compound having bidentate ligands.

9. The process of claim 8, wherein said chealate complexing compound comprises 1,3-dicarbonyl compounds, ethylenediaminetetraacetic acid, nitrilotriacetic acid or salts thereof, potassium hexacyanoferrate (III) or ethylene glycol bis(2-aminoethyl) tetraacetic acid.

10. The process of claim 9, wherein said chelate complexing compound comprises nitrilotriacetic acid or the acidic or neutral alkali metal salts thereof.

11. A process for the preparation of a macrocyclic ester or lactone by cyclizing an oligoester which is an oligoester of a dicarboxylic acid with a glycol or an oligoester of a hydroxycarboxylic acid, which comprises effecting the cyclizing reaction in the presence of a complex compound of trivalent iron.

12. The process of claim 11, wherein the macrocyclic compound has from 13 to 18 ring members.

13. The process of claim 1, wherein the linear oligoester is prepared at from about 50 to 300° C. and a pressure of from 0.01 hPa to 10 MPa.

14. The process of claim 1, wherein the cyclization reaction is carried out at a pressure from about 0.01 to 700 hPa.

15. The process of claim 1, wherein the concentration of the iron (III) complex compound is from about 0.1 to 1% by weight, based on the starting materials in the first stage.

16. The process of claim 1, which is carried out batchwise or continuously.

17. The process of claim 1, wherein said macrocyclic ester produced is ethylene glycol dodecanedioate.

18. The process of claim 1 which comprises reacting with heating in a first stage dimethyl dodecanedioate with ethylene glycol in the presence of the monosodium salt of the iron (III) ethylenediaminetetraacetic acid complex to prepare a reaction mixture comprising an oligoester of mean molecular weight melting from 40 to 50° C. and in a second stage heating the oligoester to prepare cyclic ethylene glycol dodecanedioate.

19. The process of claim 1 which comprises reacting with heating in a first stage dimethyl brassylate with ethylene glycol in the presence of tris(2,5-pentadianato) iron (III) to prepare a reaction mixture comprising an oligoester melting from 40 to 50° C. and in a second stage heating the oligoester to prepare cyclic ethylene glycol brassylate.

20. The process of claim 1 which comprises reacting with heating in a first stage 15-hydroxypentadecanoic acid in the presence of the monosodium salt of the iron (III) ethylenediaminetetraacetic acid complex to prepare an oligoester and in a second stage heating the oligoester to prepare cyclopentadecanolide.

* * * * *